United States Patent [19]

Jubran et al.

[11] Patent Number: 5,670,446

[45] Date of Patent: Sep. 23, 1997

[54] SULTINE COLOR-FORMER COMPOUNDS AND THEIR USE IN CABONLESS COPY PAPER

[75] Inventors: Nusrallah Jubran, St. Paul, Minn.; Alan R. Katritzky, Gainesville, Fla.; Josef V. Ugro, Jr., Mahtomedi, Minn.

[73] Assignee: Minnesota Mining and Manufacturing Company, St. Paul, Minn.

[21] Appl. No.: 656,937

[22] Filed: May 30, 1996

[51] Int. Cl.$^6$ .......................... B41M 5/136; B41M 5/145
[52] U.S. Cl. .......................... 503/201; 427/152; 503/215; 503/218; 503/220
[58] Field of Search .......................... 427/150–152; 503/218, 220, 215, 201, 226

[56] References Cited

U.S. PATENT DOCUMENTS

| | | | |
|---|---|---|---|
| 3,301,870 | 1/1967 | Terzijska | 260/326.3 |
| 4,020,232 | 4/1977 | Kohmura et al. | 502/218 |
| 4,929,411 | 5/1990 | Usami et al. | 503/213 |
| 5,324,619 | 6/1994 | Kawabe et al. | 430/191 |

FOREIGN PATENT DOCUMENTS 6297839  10/1994  Japan .................... 503/218

OTHER PUBLICATIONS

Katritzky et al., "Directed Metalation of Benzenesulfinamides. A Novel Route to Meta–Substituted Aromatic Compounds," *J. Org. Chem.*, 55, pp. 74–78 (1990).

*Primary Examiner*—Bruce H. Hess
*Attorney, Agent, or Firm*—Susan Moeller Zerull

[57] ABSTRACT

This invention includes novel sultine compounds and the reaction of these compounds to form colored compounds. The invention also includes the use of these color-forming compounds in the manufacture and imaging of thermal imaging papers and pressure-sensitive imaging papers.

12 Claims, No Drawings

SULTINE COLOR-FORMER COMPOUNDS AND THEIR USE IN CABONLESS COPY PAPER

FIELD OF THE INVENTION

This invention relates to novel sultine color-forming compounds; the reaction of these compounds to form colored compounds; and the use of these color-forming compounds in the manufacture and imaging of thermal imaging papers and pressure-sensitive imaging papers.

BACKGROUND OF THE ART

Color forming compounds are useful in a wide variety of products, including carbonless papers. Products using color-forming compounds frequently comprise at least two reactants, a color-forming compound and a developer, and a means for preventing premature reaction of the reactants.

Carbonless paper imaging finds application in such areas as credit card receipts and multipart forms. Carbonless paper imaging involves forming an image by the application of pressure to the carbonless paper. For carbonless paper products, one of the reactants is typically encapsulated to prevent premature reaction of the color-forming compound with the developer. Preferably, a fill solution of the color-forming compound or compounds in a hydrophobic solvent is encapsulated or contained in microcapsules. When activating pressure is applied to the carbonless paper, such as from a stylus or a typewriter key, the capsules rupture, the solution of encapsulated color-forming compound is released, and a reaction between the previously separated reactants occurs. In general, the resulting reaction will form a colored image corresponding to the path traveled by the stylus or the pattern of pressure provided by the stylus or key.

A common construction has a top sheet referred to as a donor sheet or coated back sheet (CB). Preferably, the material coated on the backside comprises a suitable binder and microcapsules containing color-forming compounds and solvent. This top sheet is used in conjunction with a second sheet, known as a receptor or developer sheet, that is coated on the frontside (CF). The coating on the frontside of the second sheet comprises a developer, optionally in a suitable binder. The term "suitable binder" refers to a material, such as starch or latex, that allows for dispersion of the reactants in a coating on a substrate.

The two sheets are positioned such that the backside of the donor sheet faces the developer coating on the front side of the receptor sheet. In many applications the front surface of the donor (CB) and receptor (CF) sheets contain preprinted information of some type and the activating pressure is generated by means of a pen or other writing instrument used in filling out the form. Thus, the image appearing on the receptor sheet is a copy of the image applied to the front side of the donor sheet. Optionally, intermediate sheets having one surface coated with the encapsulated color-forming compound, and a second, opposite surface, coated with a developer, can be placed between the CF and CB sheets. Such sheets are generally referred to herein as "CFB" sheets (i.e., coated front and back sheets). Of course, each side including color-forming compound thereon should be placed in juxtaposition with a sheet having developer thereon.

Constructions comprising at least a first substrate surface, on which is coated the encapsulated color-forming compound, and a second substrate surface, on which is coated a developer, are often referred to as a "set" or a "form-set" construction. The sheets in form-sets are typically secured to one another, e.g., as with an adhesive. In a multi-page form-set the sheets are sequenced in the order from top to bottom CB, CFB(s), and CF. This insures that in each form-set a color-forming compound and a color developer will be brought into contact when the microcapsules containing the color-forming compound are ruptured by pressure.

An alternative to the use of CB, CF, and CFB sheets is the self-contained (SC), or autogenous, carbonless paper in which both the color-forming compound and developer are applied to the same side of the sheet and/or are incorporated into the fiber lattice of the paper sheet. See e.g., European Patent Application 627 994 A1. Self-contained carbonless paper sheets are frequently used as the second and additional sheets in form-sets.

Color-forming compounds useful in carbonless paper products preferably should be capable of being encapsulated. A wide variety of processes exist by which microcapsules can be manufactured and a wide variety of capsule materials can be used in making the capsule shells, including gelatin and synthetic polymeric materials. Three methods that have achieved commercial utility are referred to as in-situ polymerization, interfacial polymerization, and coacervation encapsulation. Popular materials for shell formation for in-situ polymerization include the product of the polymerization reaction between such materials as urea and formaldehyde (UF capsules), melamine and formaldehyde (MF capsules), and monomeric or low molecular weight polymers of dimethylolurea or methylolated urea and aldehydes. Popular materials for interfacial polymerization include reaction of a polyisocyanate with a polyamine. The preparation of capsules by in-situ and interfacial polymerization and of carbonless sheets employing these capsules is disclosed in European Patent Application 0 539 142 A1. Popular materials for shell formation using coacervation polymerization include gelatin, albumin, starch, agar, carboxymethylcellulose, gum arabic, and mixtures of these materials.

In addition, the color-forming compound should be soluble and non-reactive with the fill solvent used for the encapsulation, insoluble in the aqueous solution used as the dispersing phase, non-reactive with other color-forming compounds present in the encapsulation medium, and non-reactive with the materials used to form capsule walls. Finally, the color-forming compound preferably forms a stable colored image nearly instantaneously upon contact with a receptor sheet. The color reaction helps ensure creation of an accurate, almost instantly readable copy. The stability of the colored image is important because an image that fades over time is generally undesirable.

In addition to their use in carbonless paper, color-forming compounds are used in thermal imaging constructions. These elements rely on the use of heat to produce an image. Thermal imaging constructions generally comprise a support, such as paper, glass, plastic, metal, etc., coated with (a) an acid developable color-forming compound; (b) an acidic developer; and (c) binder. At elevated temperatures the developer reacts with the acid developable color-forming compound to form a colored image corresponding to the pattern in which heat was applied to the thermal imaging construction. The image may be applied by contacting the imaging construction with a thermal print head or by other heating means. Typically, the activating temperature is in the range from 60° to 225° C.

Commonly used classes of color-forming compounds for carbonless paper applications and thermal imaging include fluorans, rhodamines, and triarylmethane lactone color-forming compounds. All of these compounds react with acidic developers, such as Lewis acids, salicylic acids, phenolic compounds, or acidic clays, to form highly colored species by the opening of a lactone ring. Specific, examples of such compounds are Pergascript Black I-R (a fluoran) and crystal violet lactone (a triarylmethane lactone). Unfortunately, the color image formed with most of these color-formers fade over time, especially with exposure to air and/or sunlight. Therefore, a more permanent color forming reaction is desired.

SUMMARY OF THE INVENTION

One aspect of this invention is a class of novel sultine color-forming compounds having the central nucleus:

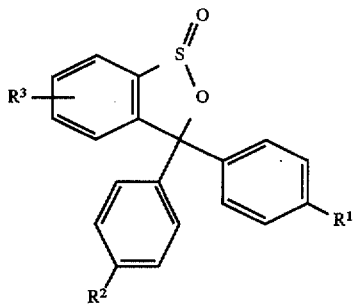

wherein $R^1$, $R^2$, and $R^3$ are independently selected from the group consisting of hydrogen, alkyl groups of up to 20, preferably up to 10, carbon atoms, cycloalkyl groups of up to 20, preferably up to 10, carbon atoms, amino groups, and strongly electron donating groups, provided that at least one of $R^1$, $R^2$, and $R^3$ is an amino group and at least one of the remaining substituents $R^1$, $R^2$, and $R^3$ is a strongly electron donating group. In other words, each compound must have one amino substituent and a second substituent which is a strongly electron donating group. Examples of strongly electron donating groups include hydroxy, alkoxy and alkylthio groups of up to 10 carbon atoms, and amino groups. The preferred amino groups have the formula $NR^4R^5$, wherein $R^4$ and $R^5$ are independently selected from the group consisting of hydrogen, alkyl groups of up to 20 carbon atoms, alkenyl groups of up to 20 carbon atoms, and aryl groups of up to 14 carbon atoms; or $R^4$ and $R^5$ of each $NR^4R^5$ group may represent the necessary atoms to complete a 5-, 6-, or 7-membered heterocyclic ring group; or one or more $R^4$ and $R^5$ of each $NR^4R^5$ group may represent the atoms necessary to complete a 5- or 6-membered heterocyclic ring group fused to the phenyl ring on which the $NR^4R^5$ group is attached.

Another aspect of this invention is a composition comprising a sultine color-forming compound carried in a solvent.

Another aspect of this invention is a composition comprising a sultine color-forming compound and a solvent, wherein the solvent and the sultine color-forming compound are encapsulated in a substantially impermeable, pressure-rupturable microcapsule.

Also included as an aspect of this invention is a substrate with at least one surface having a coating comprising microcapsules which contain a composition comprising a sultine color-forming compound. Preferably the composition in the microcapsules also comprises a solvent.

The invention also includes an imaging construction comprising:

a first substrate having a front and back surface;
coated on at least one of the front and back surfaces of the first substrate, a sultine color-forming compound;
a developer compound; and
a means for separating the color-forming compound from the developer compound until the construction is subjected to activating pressure.

Preferably, the construction comprises:
a first substrate having a from and back surface;
coated on the back surface of the first substrate, a sultine color-forming compound;
a second substrate having a from and back surface;
coated on the front surface of the second substrate, a developer compound; and
a means for separating the sultine color-forming compound from the developer compound until the construction is subjected to activating pressure.

In this construction, the first and second substrates are positioned so that the back of the first substrate contacts the front surface of the second substrate. The construction may also comprise additional substrates that have front and back surfaces, the back surface being coated with the sultine color-forming compound and the front surface being coated with the developer. These substrates are positioned between the first and second substrates in such a manner that a surface bearing a color-forming compound on one substrate contacts a surface beating a developer on another substrate. This imaging construction may be referred to as a form-set carbonless imaging construction employing CB and CF sheets and optionally CFB substrates or sheets.

Alternatively, the imaging construction comprises:
a first substrate having a front and back surface;
a second substrate having a front and back surface;
coated on the front surface of the second substrate, a sultine color-forming compound; and a developer compound; and
means for separating the color-forming compound from the developer compound until the construction is subjected to activating pressure.

In this construction, the first and second substrates are positioned so that the back of the first substrate contacts the front surface of the second substrate. The construction may also comprise additional substrates that have front and back surfaces, the front surface being coated with both the color-forming compound and the developer. These substrates are positioned between the first and second substrates in such a manner that a surface bearing a color-forming compound and developer on one substrate contacts the back surface on another substrate. This imaging construction may be referred to as a form-set carbonless imaging construction employing self-contained (SC) substrates or sheets.

In both constructions, the preferred means for separating the color-forming compound from the developer is by locating one of the reactants, preferably the color-forming compound, within a pressure-rupturable microcapsule.

The invention also includes within its scope a method of forming an image comprising providing an imaging construction as described above and applying pressure to the imaging construction thereby enabling the color-forming compound and the developer to react to form a colored image.

An alternative method of forming an image within the scope of this invention comprises providing an imaging construction comprising a substrate, a sultine color-forming compound, and an acidic developer, and applying heat to the construction in an imagewise manner thereby causing the color-forming compound to react with the developer to create a colored image. The thermographic imaging construction used to form this image by the application of heat is also within the scope of this invention. A variety of means may be used to separate the color-forming compound from the developer until heating. One suitable means of separating the color-forming compound from the developer is by having insolubility of these active ingredients in the coating. Melting of the coating then allows the two active ingredients to come into contact and react.

As used herein:

The term "activating pressure" means a pressure sufficient to cause the color-former to contact and react with the developer.

When a general structure is referred to as "a compound having the central nucleus" of a given formula, any substitution which does not alter the bond structure of the formula or the shown atoms within that structure is included within the formula. For example, in compounds of the structure shown above substituent groups may be placed on the aromatic rings, but the basic structure shown may not be altered and the atoms shown in the structure may not be replaced. When a general structure is referred to as "a general formula" it does not specifically allow for such broader substitution of the structure.

$R^1$, $R^2$, $R^3$, $R^4$, and $R^5$ in the foregoing-disclosed formulae may contain additional substituent groups. As is well understood in this area, substitution is not only tolerated, but is often advisable and substitution is anticipated on the compounds used in the present invention. As a means of simplifying the discussion and recitation of certain substituent groups, the terms "group" and "moiety" are used to differentiate between those chemical species that may be substituted and those which may not be so substituted. Thus, when the term "group," such as "aryl group," is used to describe a substituent, that substituent includes the use of additional substituents beyond the literal definition of the basic group. Where the term "moiety" is used to describe a substituent, only the unsubstituted group is intended to be included. For example, the phrase, "alkyl group" is intended to include not only pure hydrocarbon alkyl chains, such as methyl, ethyl, propyl, t-butyl, cyclohexyl, iso-octyl, octadecyl and the like, but also alkyl chains bearing substituents known in the art, such as hydroxyl, alkoxy, phenyl, halogen atoms (F, Cl, Br, and I), cyano, nitro, amino, carboxy, etc. For example, alkyl group includes ether groups (e.g., $CH_3$—$CH_2$—$CH_2$—O—$CH_2$—), haloalkyls, nitroalkyls, carboxyalkyls, hydroxyalkyls, sulfoalkyls, etc. On the other hand, the phrase "alkyl moiety" is limited to the inclusion of only pure hydrocarbon alkyl chains, such as methyl, ethyl, propyl, t-butyl, cyclohexyl, iso-octyl, octadecyl, and the like. Substituents that react with active ingredients, such as very strongly electrophilic or oxidizing substituents, would of course be excluded by the ordinarily skilled artisan as not being inert or harmless.

Other aspects, advantages, and benefits of the present invention are apparent from the detailed description, examples, and claims.

DETAILED DESCRIPTION OF THE INVENTION

The sultine color-formers of this invention may be synthesized as described below. Sulfinamides are prepared by reacting sulfinyl chlorides with amines of by treatment of thionylamines with an appropriate Gignard reagent. The resulting sulfinamides may then be treated with an alkyl-lithium compound, such as n-butyllithium to form a dianion. The dianion is reacted with a ketone to give the sultine.

Scheme I exemplifies this synthesis for the preparation of Sultine 3 using bromobenzene and Michier's ketone ($R^1$ and $R^2=N(CH_3)_2$; $R^3=H$).

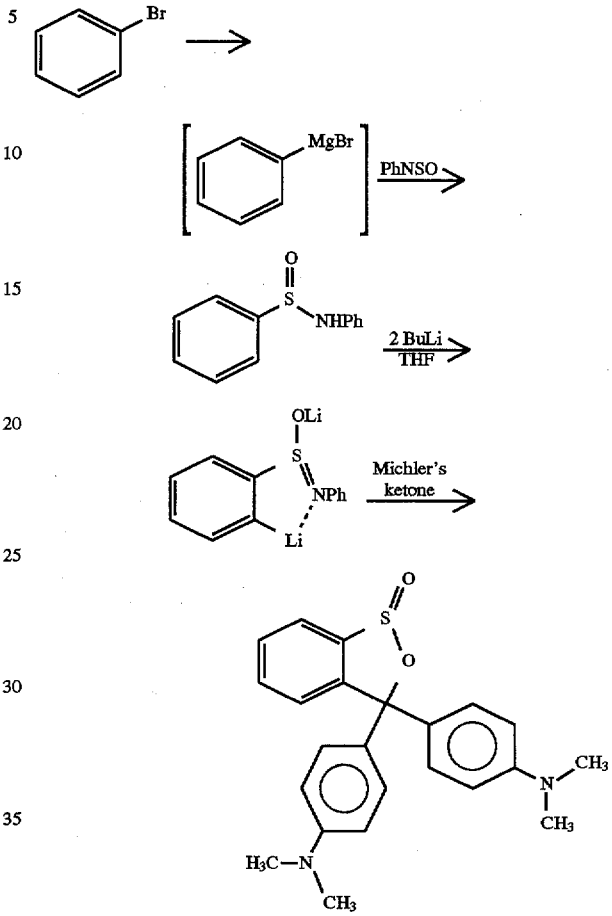

The sultine compounds are generally colorless to lightly colored, and impart little or no color to the substrates upon which they are coated. In addition, these compounds rapidly form stable, intense colors upon reaction with the developer systems typically used in carbonless papers. Finally, sultine color-forming compounds satisfy the requirements of solubility in suitable solvents for encapsulation, non-solubility in aqueous media, non-reactivity with fill solvents, and color-forming compounds mixed therewith, and compatibility with existing carbonless paper developer systems.

In some instances a mixture of color forming compounds may be used and images of varying colors can be formed by the reaction between a developer and the color-forming compounds. Appropriate mixtures to form black images are particularly useful. In systems where the color-forming compounds are encapsulated, the system may provide either one type of capsule containing a mixture of color-forming compounds or may comprise a mixture of capsules, each containing a separate encapsulated color-forming compound solution. In the latter instance, color is formed by the mixing of the color-forming compounds upon capsule rupture and reaction with the developer.

The color-forming compounds of this invention can be encapsulated by means of aminoplast polymerization encapsulation. The encapsulation process requires the color-forming compound be dissolved in a solvent or mixed solvents. Thus, the preferred sultine color-forming compounds must be soluble in the solvents used in the encapsulation process. These solvents become the fill solvents. Such solvents are aqueous immiscible solvents and include but are not limited to xylene, toluene, cyclohexane, diethyl phthalate, tributyl phosphate, benzyl benzoate, diethyl adipate, butyl diglyme, and the like. Suitable solvents are also commercially available under the brands Sure Sol™ (from Koch Refining Co.) and Norpar™ (from Exxon Chemical Americas). Preferably, the color-forming compound is present in the microcapsules in an amount from about 0.2 to about 10% by weight based on weight of the fill of the microcapsule.

Representative sultine color-former compounds useful in the present invention are shown below. These representations are exemplary and are not intended to be limiting.

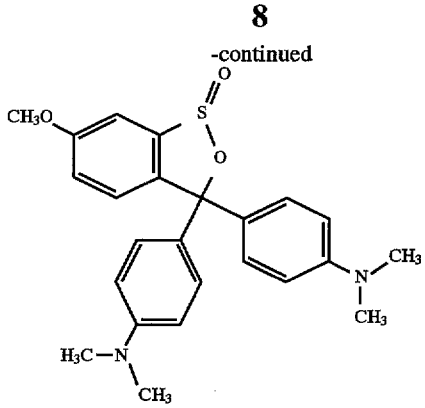

Crystal Violet Sultine-Sultine 1

Sultine 2

Sultine 3

Sultine 4

Sultine 5

Sultine 6

As noted above, sultine compounds form a colored sulfinate species when in the presence of a Lewis Acid. The sulfinate (—$SO_2^-$) species is believed to have the following general formula:

One of the characteristics of the sultine color-formers is their high extinction coefficient when compared with other commonly used color-formers. The absorption wavelength (λmax) and extinction coefficient (ε) of sultines and two comparative compounds are shown below.

| Compound | λmax (HOAc)-nm | ε-L/mol-cm |
|---|---|---|
| Sultine 1 | 607.5 | 487,000 |
| Sultine 2 | 619.5 | 128,000 |
| Sultine 3 | 622.5 | 92,000 |
| Sultine 4 | 625.0 | 305,000 |
| Comparative Compounds | | |
| Crystal Violet Lactone | 589.0 | 44,100 |
| CAS [34372-72-0] | 436.5 | 202,000 |
| leuco green fluoran | 463.5 | 91,000 |
| color-former | 609.5 | 173,000 |

Carbonless Imaging Constructions

The sultine compounds may be used in both self-contained and CB/CF carbonless paper constructions.

A preferred construction comprises the encapsulated sultine color-forming compounds dissolved in an appropriate solvent or solvents within microcapsules. The microcapsules are coated onto a back side of a donor sheet, preferably in a suitable binder. The developer, optionally in a suitable binder, is coated onto a front side of a mating, or receptor, sheet. In imaging, the two sheets are positioned such that the back side of donor sheet faces the developer coating on the front side of the receptor sheet. To create a form-set, the two sheets are secured to each other such as by an adhesive along one edge. When activating pressure is applied to the front side of the donor sheet, the capsules rupture and release the color-forming compound for transfer to the receptor sheet, forming a colored pattern due to reaction with the acidic developer. If desired, one or more additional substrates that are coated on one side with a developer and coated on the other side with the color-forming compound may be used between the previously mentioned donor and receptor sheets.

When used in a carbonless copy-paper construction, a substrate is coated with a slurry comprising microcapsules filled with a sultine color-forming compound (or mixtures thereof) dissolved in a suitable fill solvent or solvents, preferably a hydrophobic solvent such that the solution is water-insoluble. The shell of the capsules can be a water-insoluble aminoplast resin formed by polymerization of melamine and formaldehyde. The capsule slurry, may also be combined with a binding agent, such as aqueous sodium alginate, starch, latex, or mixtures thereof for coating on one face of the substrate. In a preferred embodiment, the back of the donor sheet is coated with the capsule slurry, and is referred to as the coated back (CB) sheet.

Alternatively, a composition comprising the sultine color-forming compounds of the present invention in a solvent can be carried by a variety of materials such as woven, non-woven or film transfer ribbons for use in impact marking systems such as typewriters and the like, whereby the color-forming compound is transferred to a record surface containing a developer by impact transfer means. Further, a composition comprising the color-forming compound and a solvent can be absorbed in a porous pad for subsequent transfer to a coreactive record surface by transfer means such as a portion of the human body, e.g., a finger, palm, foot or toe, for providing fingerprints or the like.

Electron acceptors, e.g., Lewis acids, may be used as developers for the color-forming compounds. Examples of such developers are activated clay substances, such as attapulgite, acid clay, bentonite, montmorillonite, acid-activated bentonite or montmorillonite, zeolite, hoalloysite, silicon dioxide, aluminum oxide, aluminum sulfate, aluminum phosphate, hydrated zirconium dioxide, zinc chloride, zinc nitrate, activated kaolin or any other clay. Acidic, organic compounds are also useful as developers. Examples of these compounds are ring-substituted phenols, resorcinols, salicylic acids, such as 3,5-bis($\alpha,\alpha$-dimethylbenzyl)salicylic or 3,5-bis($\alpha$-methylbenzyl) salicylic acid, or salicylic acid esters and metal salts thereof, for example zinc salts, and an acidic, polymeric material, for example a phenolic polymer, an alkylphenolacetylene resin, a maleic acid/colophonium resin or a partially or fully hydrolyzed polymer of maleic anhydride with styrene, ethylene or vinyl methyl ether, or carboxymethylene. Mixtures of the monomeric and polymeric compound mentioned may also be used. Preferred developers are Lewis acids, salicylic acids and particularly zincated salicylic acids, phenolic compounds and particularly zincated phenolic resins, and acidic clays.

Thermographic Imaging Elements

The sultine compounds are also useful color-forming compounds for thermographic imaging elements. Such elements are imaged by applying heat in an imagewise manner. Thermographic imaging elements generally comprise a substrate, a sultine color-forming compound, and electron acceptor developer, and optionally a binder. The sultine color-forming compound may be dissolved and dispersed in a binder coating on the substrate and the developer dissolved or dispersed in a second coating. Alternatively, the color-forming compound and the developer may be dispersed in one coating. According to one method, the binder softens in areas where heat is applied enabling the sultine color-forming compound to come into contact with the developer.

The thermographic imaging element can be prepared by dispersing the sultine color-forming compound, the developer, the binder, and optional additives, in an inert solvent, such as, for example, water. Thermographic solutions or dispersions used in this invention can be coated by various coating procedures including wire wound rod coating dip coating air knife coating curtain coating or extrusion coating. Typical wet thickness of the solution or dispersion layer can range from about 10 to about 100 micrometers (μm), and the layer can be dried in forced air at temperatures ranging from 20° C. to 100° C. The drying temperature must be less than the image activation temperature. It is preferred that the thickness of the layer be selected to provide images which give good color upon development.

Suitable binders include water-soluble or water-swellable binders including but not limited to hydrophilic polymers, such as polyvinyl alcohol, polyacrylic acid, hydroxyethylcellulose, methylcellulose, carboxymethylcellulose, polyacrylamide, polyvinylpyrrolidone, carboxylated butadiene-styrene copolymers, gelatins, starch or etherified maize starch. If the color-forming compound and the developer are present in two separate coatings, water insoluble binders, such as natural or synthetic rubber, polystyrene, styrene-butadiene copolymers, polymethyl acrylates, ethylcellulose, nitrocellulose, etc. may be used.

Suitable developers include the same electron acceptors used in pressure-sensitive papers. Examples of developers are the above mentioned day minerals and phenolic resins or phenolic compounds such as 4-tert-butylphenol, 4-phenylphenol, methylene-bis(p-phenylphenol), 4-hydroxydiphenyl ether, $\alpha$-naphthol, $\beta$-napthol, methyl or benzyl 4-hydroxybenzoates, 4-hydroxydiphenyl sulfone, 4-hydroxyacetophenone, 2,2'-dihydroxydiphenyl, 4,4'-cyclohexylidenephenol, 4,4'-isopropylidenediphenol, 4,4'-isopropylidenebis(2-methylphenol), a pyridine complex of zinc thiocyanate, 4,4-bis(4-hydroxyphenyl)valeric acid, hydroquinone, pyrogallol, phoroglucine, p-, m-, and o-hydroxybenzoic acid, gallic acid, 1-hydroxy-2-naphthoic acid and boric acid or organic, preferably aliphatic, dicarboxylic acids, for example tartaric acid, oxalic acid, maleic acid, citric acid, citraconic acid or succinic acid.

When used in a thermographic element, the image may developed merely by heating at the above noted temperatures using a thermal stylus or print head, or by heating while in contact with a heat absorbing material. Thermographic elements of the invention may also include a dye to facilitate direct development by exposure to laser radiation. Preferably, the dye is an infrared absorbing dye and the laser is a diode laser emitting in the infrared. Upon exposure to radiation, the radiation absorbed by the dye is converted to heat which develops the thermographic element.

Determination of Color

In general, the colors formed by reaction of the color-forming compound and developer in the Examples below, were determined by preparing a 1% solution of the color-forming compound or mixture of color-forming compounds in an appropriate solvent. Unless otherwise indicated, the solvent was composed of a mixture of diethyl phthalate (50.0%), and cyclohexane (50.0%). The images were formed by applying two stripes of the solution to a 3M Scotchmark™ CF developer (receptor) sheet using a cotton tipped applicator swab. This sheet contains a zincated phenolic resin (an alkyl Novolak™ resin) as the Lewis acid developer. Complete development of the image was achieved by passing the sheet through a hot shoe adjusted to 102° C., making a revolution every 10 seconds. (Development may also be achieved by holding the sheet at room temperature for a sufficient length of time). The visually observed colors were measured and recorded.

One method of color measurement is to determine the color's position in color space. One color space system is the CIELAB System; see F. W. Billmeyer, Jr., and M. Saltzman, *Principles of Color Technology*; John Wiley & Sons; New York, N.Y.; Ch. 2 & 3, 1981. In this system three mutually perpendicular axes (L*, a*, and b*) are needed to define a color. "L*" (+z axis) represents the lightness or darkness of the image (L of 100 is white, L of 0 is black); "a*" (x axis) represents the amount of red or green (+a* is red, –a* is green); and "b*" (y axis) represents the amount of yellow or blue (+b* is yellow, –b* is blue). By measuring a material's L*, a*, and b* values, the color of one sample can be compared with that of other samples.

Because the color of a sample is also dependent upon the color temperature of the illuminating source, the angle at which the sample is illuminated, the angle at which the illumination is reflected, and the angle of the retina illuminated, these all need to be specified. Many instruments have been developed to record these values. One such instrument is the Gretag SPM-100 Spectrophotometer. This instrument is capable of automatically determining the L*, a*, and b* values for a given sample, and was used for the following examples.

The L*, a*, and b* color coordinates of the more uniform stripe were measured on a Gretag SPM-100 Spectrophotometer using no color filters, a standard Observer of 2°; and using illuminant D-50. The sample was illuminated at 45° and read at 0°. The observed (image) color and the CIELAB coordinates for the developed color-forming compounds of this invention are given for each sample.

Imaging Evaluation of Coated CB Sheets

Tests were performed on coated CB sheets to determine their characteristics and acceptability for use. These tests include evaluation of imaging speed, and ultimate image density.

Imaging speed is determined by passing a CB and a CF sheet under a steel roller with an impact pressure of approximately 350 pli (pressure per linear inch) and measuring the reflectance of the resultant image four seconds after imaging. A Photovolt Model 670 Reflectance Meter with a model 610 search unit fitted with a green filter was used. This instrument is available from Seragen Diagnostics, Inc. A presently sold product such as 3M Brand Carbonless Paper has an imaging speed of 35 to 40. In interpreting the reflectance numbers, a high number indicates high reflectance, and a low number indicates low reflectance. Thus a white surface would have a reflectance of close to 100, and a black surface would have a reflectance approaching zero. A "slower" imaging system would be expected to have a greater (higher number) reflectance after 4 seconds than a faster imaging system.

Ultimate image reflectance was also measured using the Photovolt Model 670 Reflectance Meter. Subsequent to image formation the imaged sheet was heated to 102° C. for 7 seconds to fully develop the image, and the reflectance was measured. A presently sold product such as 3M B/P Brand Carbonless Paper has an ultimate image reflectance of 24 to 28.

Objects and advantages of this invention will now be illustrated by the following examples, but the particular materials and amounts thereof recited in these examples, as well as other conditions and details, should not be construed to unduly limit this invention.

EXAMPLES

All materials used in the following examples are readily available from standard commercial sources such as Aldrich Chemical Co. (Milwaukee, Wis.) unless otherwise specified. The following additional terms and materials were used.

Melting points were determined with a Kofler hot stage apparatus and are uncorrected. $^1$H nmr and $^{13}$C nmr spectra were recorded on a Gemini VXR 300 MHz spectrometer in deuterochloroform using tetramethylsilane as an internal reference for $^1$H spectra and deuterochloroform for $^{13}$C spectra. Elemental analyses were performed on a Carlo Erba-1106 instrument.

Color measurements were made on a Gretag SPM-100 Spectrophotometer. This instrument is available from Gretag Aktiengesellschaft, Regensdorf Switzerland.

All percentages are by weight unless otherwise indicated.

AE 700 is a di-$C_6$ to $C_8$ branched alkyl ester of 1,2-benzenedicarboxylic acid. It has CAS Registry No [71888-89-6], and is available from Exxon Chemical Americas, Houston, Tex.

Luracol™ is a partially methylated, methylolated melamine formaldehyde resin and is available from BASF Corp.

Lupasol™ PA-140 is an arylamidosulfonic acid, sodium salt and is available from BASF Corp.

Norpar™ 12 is a liquid paraffinic hydrocarbon. It has CAS Registry No [64771-72-8], and is available from Exxon Chemical Americas, Houston, Tex.

Pergascript™ Red I-6B, Pergascript™ Orange I-5R, and Pergascript™ Black I-R are fluoran color-forming compounds available from Ciba-Geigy, Greensboro, N.C.

Sure Sol™ 290 [CAS RN 81846-81-3] is a 4,4'-bis-butylated-1,1'-biphenyl and is available from Koch Refining Co., Corpus Christi, Tex.

Crystal Violet Lactone is 3,3'-bis(p-dimethylaminophenyl)-6-dimethylaminophthalide and has CAS Registry No. [1552-42-7]. It has the structure shown below:

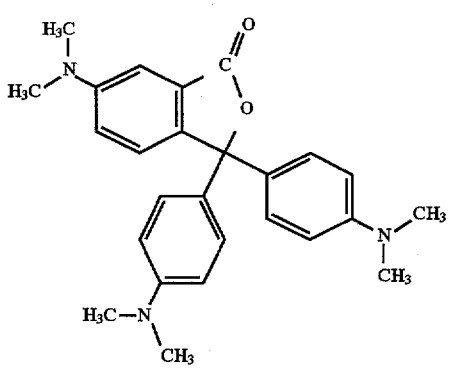

Crystal Violet Lactone (CVL)

The Leuco Green Fluoran Color-Former is 3'-(diethylamino)-7'-(dibenzyl-amino)-6'-(diethylamino) fluoran. CAS [34372-72-0].

The following comparative compounds were also prepared and evaluated.

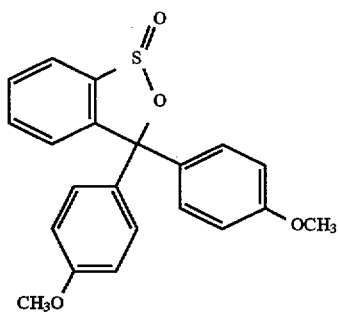

Comparative Sultine 7

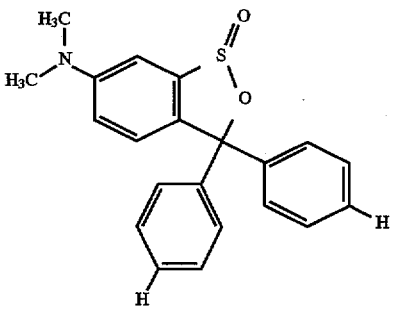

Comparative Sultine 8

Preparation of Sultine Color-Formers

Preparation of sultines 1, 2, 3, 4, 6, 7, and 8 by lithiation of N-phenyl-benzenesulfinamide: To a stirred solution of the appropriately substituted N-phenyl-benzenesulfinamide (10 mmol) in THF (70 mL) at −5° C. to 0° C. was added butyllithium (20 mmol). The solution was stirred at this temperature for 2 hours. Then a solution of ketone in THF (80 mL) was added slowly. The mixture was kept at this temperature for 1 hour then at room temperature overnight. Aqueous NH$_4$Cl (10%) was added and the solution extracted with ethyl acetate (2×100 mL), dried with MgSO$_4$ and evaporated to give a residue. The pure product was obtained by column chromatographic separation on silica gel (hexane/ethyl acetate—3:1).

Preparation of Sultine 1: Preparation of N,N-dimethyl-3-bromoaniline: A mixture of 3-bromoaniline (100 mmol) and dimethyl sulfate (250 mmol) was heated in an oil bath under nitrogen at 110° C. for 48 hours. Aqueous KOH (300 mmol) was added, the reaction mixture stirred for an additional 1 hour, and then extracted with chloroform (3×50 mL). The organic layer was washed with water, dried over anhydrous magnesium sulfate, filtered, and the solvent was removed at reduced pressure. The residue was chromatographed with hexane:ethyl acetate (5:1) to afford N,N-dimethyl-3-bromoaniline in 70% yield. H-NMR, C-NMR, IR and elemental analysis confirmed the structure.

N-Phenyl-3-(dimethylamino)benzenesulfinamide: A solution of N,N-dimethyl-3-bromoaniline (20 mmol) in dry THF (60 mL) was added dropwise to magnesium turnings and a trace of iodine at room temperature. The mixture was heated under reflux for 4 hours to give the Grignard reagent.

This Grignard reagent was added at ca. −10° C. to a solution of N-thionylaniline (15 mmol) in dry diethyl ether (50 mL). The mixture was stirred at this temperature for 30 minutes then at room temperature for 10 hours. The reaction was then quenched with aqueous NH$_4$Cl (10%), extracted with ether (3×50 mL) and dried over MgSO$_4$. Evaporation of the solvent gave a residue, which was chromatographed on silica gel (hexane:ethyl acetate, 3:1) to afford N-phenyl-3-(dimethylamino)benzenesulfinamide. Yield: 60%. mp 86°-87° C. δ$_H$ (300 MHz; CDCl$_3$; Me$_4$Si) 2.98 (6H, s), 6.32 (1H, s), 6.80 (1H, m), 6.99-7.11 (5H, m), 7.23-7.32 (3H, m). δ$_C$ (75 MHz; CDCl$_3$) 40.3, 108.0, 112.5, 114.7, 118.5, 123.2, 129.4, 129.7, 141.0, 150.8.

Anal: Calcd for C$_{14}$H$_{16}$N$_2$OS: C, 64.59; H, 6.20; N, 10.77. Found: C, 64.32; H, 6.23; N, 10.69.

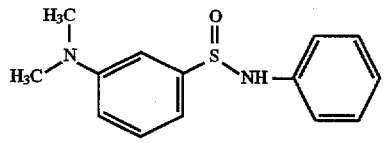

Sultine 1—6-Dimethylammino-3,3-bis-(4-dimethylamino)phenyl-3H-2,1-benzoxathiole 1-oxide: To a stirred solution of N-phenyl-3-(dimethylamino) benzenesulfinamide (7.4 mmol) in THF (60 mL) at −30° C. was added n-BuLi (14.8 mmol). The solution was warmed to 0° C. and stirred for 2 hours, and then was cooled to −78° C. Michler's ketone (4,4'-bis-(dimethylamino) benzophenone; 7.4 mmol) dissolved in 50 mL of THF was added slowly. The reaction mixture was kept at −78° C. for a few hours and allowed to warm to room temperature overnight. Aqueous HCl (10%) was added to quench the reaction. The solution was neutralized with aqueous Na$_2$CO$_3$ then extracted with ethyl acetate (2×60 mL) and dried over anhydrous magnesium sulfate. After evaporation of solvent, the residue was chromatographed on silica gel and eluted with ethyl acetate to give the desired Crystal Violet Sultine (Sultine 1). $^1$H-NMR, $^{13}$C-NMR, IR and elemental analysis confirmed the structure.

Sultine 1—6-Dimethylamino-3,3-bis-(4-dimethylamino) phenyl-3H-2,1-benzoxathiole 1-oxide: Yield 34%; Mp 183°-184° C.; δ$_H$ (300 MHz; CDCl$_3$; Me$_4$Si) 2.91 (s, 12H), 2.98 (s, 6H), 6.63 (d, 4H, J9.0), 6.85 (dd, 1H, J8.6, 2.5), 6.92 (d, 1H, J2.4), 7.14 (d, 2H, J8.6), 7.13-7.23 (m, 3H); δ$_C$ (75 MHz; CDCl$_3$) 40.3, 40.5, 105.1, 111.6, 116.4, 125.4, 128.7, 131.0, 131.4, 147.8, 150.0, 151.2. (Found: C, 68.77; H, 6.75; N, 9.57. Calc. for C$_{25}$H$_{29}$N$_3$O$_2$S: C, 68.93; H, 6.72; N, 9.65).

Sultine 2—6-Methyl-3,3-bis-(4-dimethylamino)phenyl-3H-2,1-benzoxathiole 1-oxide-: Yield 41%. Mp 100°-103°

C.; $\delta_H$ (300 MHz; CDCl$_3$; Me$_4$Si) 2.39 (s, 3H), 2.89 (s, 12H), 6.61 (d, 4H, J8.8), 7.29 (br s, 4H), 7.31 (d, 2H, J 7.9), 7.49 (s, 1H); $\delta_C$ (75 MHz; CDCl$_3$)20.9, 40.2, 106.1, 111.4, 123.6, 124.9, 128.6, 132.0, 132.9, 139.4, 141.4, 146.5, 150.0. (Found: C, 70.88; H, 6.56; N, 7.00. Calc. for C$_{24}$H$_{26}$N$_2$O$_2$S: C, 70.91; H, 6.45; N, 6.90).

Sultine 3—3,3-bis-(4-Dimethylamino)phenyl-3H-2,1-benzoxathiole 1-oxide: Yield 48%. Mp 174°–176° C.; $\delta_H$ (300 MHz; CDCl$_3$; Me$_4$Si) 2.90 (s, 12H), 6.62 (4H, d, J8.9), 7.20 (br s, 4H), 7.32–7.35 (m, 1H), 7.46–7.51 (m, 2H), 7.70–7.73 (m, 1H); $\delta_C$ (75 MHz; CDCl$_3$) 40.2, 106.3, 111.5, 123.7, 125.3, 128.7, 129.1, 131.8, 144.1, 146.3, 150.1. (Found: C, 70.23;H, 6.31;N, 7.01. Calc. for C$_{23}$H$_{24}$N$_2$O$_2$S: C, 70.38; H, 6.17; N, 7.14).

Sultine 4—6-Methoxy-3,3-bis-(4-dimethylamino)phenyl-3H-2,1-benzoxathiole 1-oxide: Yield 30%; Mp 85°–87° C.; $\delta_H$ (300 MHz; CDCl$_3$; Me$_4$Si) 2.91 (s, 12H), 3.60 (s, 3H), 6.62 (d, 4H, J9.1), 6.96 (d, 1H, J8.1), 7.18–7.33 (m, 4H), 7.46 (t, 2H, J7.90); $\delta_C$ (75 MHz; CDCl$_3$) 40.1, 55.7, 107.9, 111.0, 114.9, 115.6, 128.3, 129.5, 131.5, 148.1, 149.9, 154.8. (Found: C, 67.81; H, 6.41; N, 6.25. Calc. for C$_{24}$H$_{26}$N$_2$O$_3$S: C, 68.22; H, 6.21; N, 6.63).

Sultine 6—6-Dimethylamino-3,3-bis-(4-methoxy) phenyl-3H-2,1-benzoxathiole 1-oxide: Yield 60%; Mp 77°–79° C.; $\delta_H$ (300 MHz; CDCl$_3$; Me$_4$Si) 2.90 (s, 6H), 3.67 (s, 3H), 3.69 (s, 3H), 6.77–6.89 (m, 6H), 7.11–7.18 (m, 3H), 7.34 (d, 2H, J8.6); $\delta_C$ (75 MHz; CDCl$_3$) 40.0, 54.8, 54.9, 104.2, 104.6, 113.0, 113.1, 116.1, 125.1, 128.5, 128.7, 130.0, 134.9, 135.5, 147.4, 151.0, 158.8, 159.2. (Found: C, 67.53; H, 5.64; N, 3.29. Calc. for C$_{23}$H$_{23}$NO$_4$S: C, 67.46; H, 5.67; N, 3.42).

Comparative Sultine 7—3,3-bis-(4-Methoxy)phenyl-3H-2,1-benzoxathiole 1-oxide: Obtained as an oil. Yield 74%; $\delta_H$ (300 MHz; CDCl$_3$; Me$_4$Si) 3.73 (s, 3H), 3.75 (s, 3H), 6.82 (d, 4H, J7.1), 7.13 (d, 2H, J8.7), 7.33 (d, 3H, J9.1), 7.46–7.58 (m, 2H), 7.74 (d, 1H, J7.9); $\delta_C$ (75 MHz; CDCl$_3$) 54.9, 55.0, 104.6, 113.3, 113.4, 123.7, 125.1, 128.7, 128.9, 129.4, 131.9, 134.1, 134.6, 143.4, 146.2, 159.2, 159.5. (Found: C, 68.61; H, 4.90; Calc. for C$_{21}$H$_{18}$O$_4$S: C, 68.84; H, 4.96).

Comparative Suultine 8—6-Dimethylamino-3,3-diphenyl-3H-2,1-benzoxathiole 1-oxide: Yield 45%; Mp 140°–142° C.; $\delta_H$ (300 MHz; CDCl$_3$; Me$_4$Si) 2.99 (s, 6H), 6.86–6.93 (m, 2H), 7.18–7.31 (m, 9H), 7.43 (dd, 2H, J 8.0, 1.3); $\delta_C$ (75 MHz; CDCl$_3$)40.4, 104.3, 105.1, 116.3, 125.5, 127.4, 127.5, 127.8, 128.1, 128.2, 128.3, 129.8, 142.9, 143.3, 147.9, 151.4. (Found: C, 72.28; H, 5.48; N, 3.97. Calc. for C$_{21}$H$_{19}$NO$_2$S: C, 72.18; H, 5.48; N, 4.01).

Sultine 5—One-pot preparation of from 4-bromo-N,N-dimethylaniline: To a solution of 4-bromo-N,N-dimethylaniline (10 mmol) in diethyl ether (50 mL) was added lithium metal (which had been cut into small pieces in ether) (0.12 g, 20 mmol) and the mixture was refluxed for 3 hours. After the solution was cooled to −5° C. to 0° C., N-thionylaniline (10 mmol) was added and stirred for 1 hour at this temperature. Then butyllithium (2.5M, 4 mL, 10 mmol) was added and the lithiation was continued for another 1 hours. Michier's ketone (4,4'-bis(dimethylamino) benzophenone) in THF (80 mL) was added slowly. The mixture was kept at this temperature for 1 hour then at room temperature overnight. Aqueous NH$_4$Cl (10%) was added and the solution extracted with ethyl acetate (2×100 mL), dried with MgSO$_4$ and evaporated to give a residue. The pure product was obtained by column chromatographic separation on silica gel (hexane/ethyl acetate—3:1). Yield 68%; Mp 182°–184° C.; $\delta_H$ (300 MHz; CDCl$_3$; Me$_4$Si) 2.90 (s, 12H), 2.93 s, 6H), 6.41 (d, 1H, J2.2), 6.63 (d, 4H, J7.5), 6.71 (dd, 1H, J8.8, 1.3), 7.14 (d, 2H, J 7.7), 7.34 (d, 2H, J=7.9), 7.51 (d, 1H, J8.7). (Found: C, 69.24; H, 6.72; N, 9.58. Calc. for C$_{25}$H$_{29}$N$_3$O$_2$S: C, 68.93; H, 6.72; N, 9.65).

Example 1

A 1% solution of each of color-formers 1–5 and comparative sultine 7 were prepared in a mixture of diethylphthalate:cyclohexane (1:1). Each solution was swabbed onto a sheet of 3M Scotchmark™ CF paper using a cotton tipped applicator swab. This CF sheet contains a zincated phenolic resin as the developer. In samples 1–5, an immediate reaction occurred. The following colors were obtained immediately after imaging and without further development with heat.

| Color-Former | Image Color | L* | a* | b* |
| --- | --- | --- | --- | --- |
| 1 | Blue | 48.07 | 8.12 | −66.07 |
| 2 | Green | 70.91 | −55.36 | −6.97 |
| 3 | Green | 71.95 | −50.79 | −13.93 |
| 4 | Green | 74.35 | −48.98 | −9.42 |
| 5 | Green | 72.54 | −41.04 | −16.05 |
| 7 | No Color | | | |

Example 2

The following example demonstrates the use of the sultines of this invention in combination with lactone color-formers to provide blue-black image. A 1% solution of a mixture of color-formers was prepared in a mixture of diethylphthalate:cyclohexane (1:1). The color-former solution had the following composition:

| Compound | wt % |
| --- | --- |
| Sultine 1 | 22% |
| Sultine 2 | 16% |
| Pergascript Red I-6B | 8% |
| Pergascript Orange I-5R | 5% |
| Pergascript Black I-R | 49% |

The solution was swabbed onto a sheet of 3M Scotchmark™ CF paper using a cotton tipped applicator swab. This CF sheet contains a zincated phenolic resin as the developer. An immediate reaction occurred to form an intense blue-black image.

| Example | Image Color | L* | a* | b* |
| --- | --- | --- | --- | --- |
| 2 | Blue-black | 54.02 | −10.54 | −13.28 |

Example 3

The following Example demonstrates the use of the color-formers of this invention in a fingerprinting system. An index finger was placed lightly onto a piece of filter paper saturated with the 1% solution of a mixture of color-formers of Example 3. The finger was then pressed against a sheet of 3M Scotchmark™ CF paper. An immediate reaction occurred to form a dark blue-black fingerprint.

Example 4

A 1% solution of sultine 1 color-former was prepared in diethylphthalate:cyclohexane (1:1). A second 1% solution of crystal violet lactone was also prepared in a mixture of diethylphthalate:cyclohexane (1:1). Each solution was swabbed onto several samples of 3M Scotchmark™ CF paper using a cotton tipped applicator swab. This CF sheet contains a zincated phenolic resin as the developer. In all cases, an immediate reaction occurred. Blue color developed in each sample immediately after imaging. The color coordinates of these samples are shown below.

|  | Initial Development | | |
| --- | --- | --- | --- |
|  | L* | a* | b* |
| Sultine 1 | 55.16 | 6.11 | −45.11 |
| CV Lactone | 51.19 | 8.18 | −47.17 |

Each imaged sample was put through a hot roll device at 215° F. (102° C.) and the color coordinates were then remeasured. The color of the sultine color-former sample changed from a deep blue color to a deep red-blue color. The color of the Crystal Violet Lactone sample did not change. The color coordinates of each sample were remeasured. The following values were obtained.

|  | After Heating | | |
| --- | --- | --- | --- |
|  | L* | a* | b* |
| Sultine 1 | 33.06 | 26.83 | −85.99 |
| CV Lactone | 51.19 | 8.18 | −47.17 |

The same color change in the sultine was observed after 90 minutes at room temperature. This color change in the sultine color-former is believed result from of oxidation from the sulfinate form to the sulfonate form.

Example 5

Freshly prepared, unheated sultine images from Example 4 were placed in a light box for three days. One half of the sample was exposed to light, the other half of the sample was covered with paper. The samples were placed on a rotating carousel about 3 inches (7.6 cm) from a circular bank of twelve 20 watt fluorescent light bulbs for three days. The color coordinates of both the covered and uncovered portions of each sample were then remeasured.

The results, shown below, demonstrate that the developed sample of crystal violet lactone that had been exposed to light faded badly. This is shown by the high L value and the low a* and b* values. The developed sample of sultine 1 that had been in the dark, turned to a deep red-blue color. The light-exposed sample of Sultine 1 retained a blue color. The following values were obtained:

|  | Initial Development | | |
| --- | --- | --- | --- |
|  | L* | a* | b* |
| Sultine 1 | 55.16 | 6.11 | −45.11 |
| CV Lactone | 51.19 | 8.18 | −47.17 |
| After Light Exposure - Covered Portion | | | |
| Sultine 1 | 33.06 | 26.83 | −85.99 |
| CV Lactone | 51.19 | 8.18 | −47.17 |
| After Light Exposure - Uncovered Portion | | | |
| Sultine 1 | 56.57 | 0.68 | −16.24 |
| CV Lactone | 77.58 | −3.07 | −7.60 |

Example 6

The developed, heated samples of sultine color-former and crystal violet lactone color-former prepared in Example 4 were heated in an oven at 120° F. (49° C.) for one week. No further color change in the samples was observed. Both images displayed good stability over this time at this temperature.

Example 7

The following Example demonstrates that compounds of this invention can be encapsulated and coated to prepare a carbonless paper form-set construction.

Encapsulation of Compound 1: A 35 g capsule fill solution containing 0.3 wt % of Crystal Violet Sultine (1) color-former in a 75:25 wt % mixture of AE 700:Norpar™ 12 was prepared.

Into a 4 oz (118 mL) glass bottle were placed 6.9 g of Luracol, 39.9 g of water, and 6.4 g of a 20% solution of Luprasol PA-140. The pH was adjusted to 3.60 with dilute sulfuric acid. A capsule fill solution (31 g) containing 0.3 wt % of Crystal Violet Sultine color-former in a 75:25 wt % mixture of AE 700:Norpar 12 was added. A Silverson mixer L4R was immersed in the mixture and the mixture stirred at a setting of 3.2. After 5 minutes, the pH remained at 3.60. Due to the energy of the mixing, the temperature rose to approximately 55° C. after about 20 minutes. After 90 minutes the temperature was still about 57° C. Inspection of an aliquot under a microscope showed stable capsules had formed. The Silverson mixer was removed, the jar was placed on a hot plate, stirred with a marine propeller stirrer. Heating and stirring for 90 minutes at 60° C. was followed by cooling and addition of aqueous ammonium hydroxide solution to bring the pH to approximately 8.5.

The capsules obtained were spherical with a median volumetric diameter of 6.77 μm. They had a slight indentation in one portion of the wall. The capsule dispersion contained approximately 40% capsules. The capsule slurry was used to prepare CB sheets without further modification.

Various amounts of capsule slurry were added to 65 g of a 1.5% aqueous sodium alginate solution. The mixture was applied to a coated paper using a bar coater with a 3 mil (76.2 mm) gap. The coating was allowed to dry at room temperature for 1 hour.

The coated CB sheet was imaged using a 3M Scotchmark™ CF sheet containing a zincated phenolic resin as the developer. Image color, speed, ultimate image reflectance, and L*, a*, and b* were determined as described above. The L*, a*, b* values for this Example are slightly different from those of the Examples above as the concentrations of color-forming compound are different.

| Amount capsule slurry | Speed | Ultimate | Image Color | L* | a* | b* |
| --- | --- | --- | --- | --- | --- | --- |
| 2 g | 73.40 | 67.8 | Blue | 87.86 | −2.96 | −4.61 |
| 4 g | 66.00 | 60.95 | Blue | 82.52 | −4.71 | 11.40 |
| 6 g | 64.00 | 57.45 | Blue | 80.11 | −5.23 | 15.27 |
| 8 g | 58.00 | 53.25 | Blue | 77.94 | −5.53 | 18.07 |
| 10 g | 53.85 | 45.05 | Blue | 73.31 | −5.58 | 23.19 |

Example 8

The following example demonstrates the use of the color-forming compounds of this invention in a thermal imaging element.

An aqueous slurry of 1.00 g of color-forming sultine 1, 3.00 g of styrene maleic anhydride resin (Stymer S), and 96 g of water was ball milled for 24 hours.

A thermal imaging dispersion was prepared by mixing the materials shown below.

| Component | Wet Weight - g | Dry Weight - g |
|---|---|---|
| Water | 40.0 | — |
| Rice Starch | 7.20 | 7.20 |
| Cellosize QP09-L (7%) | 16.26 | 1.38 |
| Stymer S (25%) | 16.26 | 2.85 |
| Standapol ES (28%) | 0.11 | 0.03 |
| Bisphenol A (30%) | 24.54 | 7.36 |
| Slurry of 1 (1.75%) | 6.00 | 0.10 |
| Total | 105.52 | 18.92 |

Rice starch is available from Sigma Chemical Co., St. Louis, MO. 63178.
Cellosize QP09-L is available from the Specialty Chemical Division of Union Carbide, Danbury, CT 06817.
Stymer S is the sodium salt of a styrene-maleic anhydride resin. It is available from Monsanto.
Standapol ES-3 is an anionic surfactant used as a dispersing agent. It is available from Henkel Inc., Teaneck, NJ 07666.

The dispersion was coated using a wire wound rod (Meier bar) onto bond paper and dried. The thermographic element was imaged using the tip of a heated screwdriver to simulate a thermal print head. A strong blue image resulted.

Example 9

A 1% solution of each of sultine color-former 6 and comparative sultines 7 and 8 were prepared in a mixture of diethylphthalate:cyclohexane (1:1). Each solution was swabbed onto a sheet of 3M Scotchmark™ CF paper using a cotton tipped applicator swab. This CF sheet contains a zincated phenolic resin as the developer. In all cases, no color developed.

A 1% solution of $ZnCl_2$ in acetone was then swabbed over the stripe of sultine color-former on the CF sheet. The coating of sultine 6 gave an intense blue-black color. The coatings of comparative sultines 7 and 8 remained colorless.

Reasonable modifications and variations are possible from the foregoing disclosure without departing from either the spirit or scope of the present invention as defined by the claims.

What is claimed is:

1. An imaging construction comprising:

a first substrate having a front and back surface;

coated on at least one of the front and the back surfaces of the first substrate, a color-forming compound having the general formula:

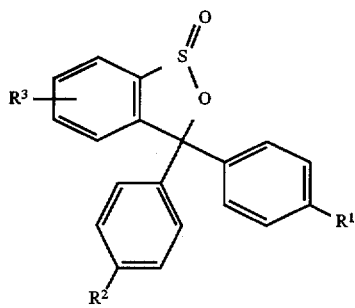

wherein $R^1$, $R^2$, and $R^3$ are independently selected from the group consisting of hydrogen, alkyl groups of up to 20 carbon atoms, cycloalkyl groups of up to 20 carbon atoms, amino groups, and strongly electron donating groups, provided that at least one of $R^1$, $R^2$, and $R^3$ is an amino group and at least one other of $R^1$, $R^2$, and $R^3$ is a strongly electron donating group;

a developer; and a means for separating the color-forming compound from the developer until the construction is subjected to activating pressure.

2. The imaging construction of claim 1 in which the strongly electron donating group is selected from the group consisting of hydroxy, alkoxy and alkylthio groups of up to 10 carbon atoms, and $NR^4R^5$, wherein $R^4$ and $R^5$ are independently selected from the group consisting of hydrogen, alkyl groups of up to 20 carbon atoms, alkenyl groups of up to 20 carbon atoms, and aryl groups of up to 14 carbon atoms; or $R^4$ and $R^5$ of each $NR^4R^5$ group may represent the necessary atoms to complete a 5-, 6-, or 7-membered heterocyclic ring group; or one or more $R^4$ and $R^5$ of each $NR^4R^5$ group may represent the atoms necessary to complete a 5- or 6-membered heterocyclic ring group fused to the phenyl ring on which the $NR^4R^5$ group is attached.

3. The imaging construction of claim 1 in which both $R^1$ and $R^2$ are $NR^4R^5$, wherein $R^4$ and $R^5$ are independently selected from the group consisting of hydrogen, alkyl groups of up to 20 carbon atoms, alkenyl groups of up to 20 carbon atoms, and aryl groups of up to 14 carbon atoms; or $R^4$ and $R^5$ of each $NR^4R^5$ group may represent the necessary atoms to complete a 5-, 6-, or 7-membered heterocyclic ring group; or one or more $R^4$ and $R^5$ of each $NR^4R^5$ group may represent the atoms necessary to complete a 5- or 6-membered heterocyclic ring group fused to the phenyl ring on which the $NR^4R^5$ group is attached.

4. The imaging construction of claim 1 wherein the means for separating the color-forming compound from the developer comprises locating one of the color-forming compound or the developer within a pressure-rupturable microcapsule.

5. The imaging construction of claim 1 wherein the color-forming compound is located within the pressure-rupturable microcapsule.

6. The imaging construction of claim 5 in which the pressure-rupturable microcapsule comprises a water-insoluble aminoplast resin formed by polymerization of melamine and formaldehyde.

7. The imaging construction of claim 1 further comprising a second substrate having a first and a second surface, wherein the color-forming compound is coated on the back surface of the first substrate and the developer is coated on the from surface of the second substrate and the first and second substrates are positioned so that the back surface of the first substrate contacts the front surface of the second substrate.

8. The imaging construction of claim 7 further comprising at least one additional substrate having a front and back surface, the back surface being coated with the color-forming compound and the front surface being coated with the developer, wherein the at least one addition substrate is positioned between the first and second substrates in such a manner that a surface bearing a color-forming compound on one substrate contacts a surface bearing a developer on another substrate.

9. The construction according to claim 1 wherein said surface of said first substrate is coated with a sultine color-forming compound and a second color-forming compound selected from the group consisting of fluoran, rhodamine, and triarylmethane lactone color-former compound.

10. A method of forming an image comprising providing the imaging construction of claim 1 and applying pressure to the imaging construction thereby enabling the color-forming compound and the developer to react to form a colored image.

11. An imaging construction comprising:

a first substrate having a front and back surface;

coated on at least one of the front and the back surfaces of the first substrate, a color-forming compound having the general formula:

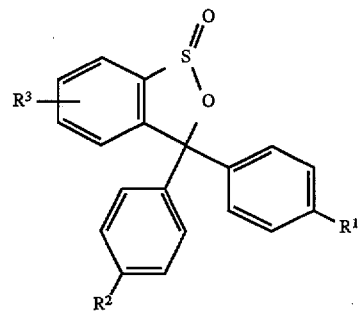

wherein $R^1$, $R^2$, and $R^3$ are independently selected from the group consisting of hydrogen, alkyl groups of up to 20 carbon atom, cycloalkyl groups of up to 20 carbon atoms, amino groups, and strongly electron donating groups, provided that at least one of $R^1$, $R^2$, and $R^3$ is an amino group and at least one other of $R^1$, $R^2$, and $R^3$ is a strongly electron donating group;

a developer; and a means for separating the color-forming compound from the developer until the construction is subjected to heat.

12. A method of forming an image comprising providing the imaging construction of claim 11 applying heat to the construction in an imagewise manner thereby causing the color-forming compound to react with the developer to create a colored image.

* * * * *

UNITED STATES PATENT AND TRADEMARK OFFICE
CERTIFICATE OF CORRECTION

PATENT NO. : 5,670,446  Page 1 of 2
DATED : September 23, 1997
INVENTOR(S) : Jubran et al It is certified that error appears in the above-identified patent and that said Letters Patent is hereby corrected as shown below:

On the title page: Item [54] and Column 1, line 2, "CABONLESS" should be --CARBONLESS--.

Col. 4, line 9, "from" should be --front--.

Col. 4, line 12, "from" should be --front--.

Col. 4, line 27, "beating" should be --bearing--.

Col. 5, line 63, "amines of by treatment" should be --amines or by treatment--.

Col. 6, line 2, "Michier's" should be --Michler's--.

UNITED STATES PATENT AND TRADEMARK OFFICE
CERTIFICATE OF CORRECTION

PATENT NO. : 5,670,446
DATED : September 23, 1997
INVENTOR(S) : Jubran et al.

It is certified that error appears in the above-identified patent and that said Letters Patent is hereby corrected as shown below:

Col. 10, line 58, "day" should be --clay--.

Col. 14, line 40, "Dimethylammino" should be --Dimethylamino--.

Col. 15, line 41, "Suultine" should be --Sultine--.

Col. 15, line 58, "Michier's" should be --Michler's--.

Col. 19, line 15, "Sluny" should be --Slurry--.

Col. 20, line 50, "the from surface" should be --the front surface--.

Signed and Sealed this

Twenty-sixth Day of May, 1998

Attest:

BRUCE LEHMAN

Attesting Officer

Commissioner of Patents and Trademarks